United States Patent
Urata et al.

(10) Patent No.: US 11,306,053 B2
(45) Date of Patent: Apr. 19, 2022

(54) ESTER COMPOUND AND LUBRICATING OIL BASE OIL

(71) Applicants: DAISAN KASEI CO., LTD, Chiba (JP); JNC CORPORATION, Tokyo (JP)

(72) Inventors: Yasuo Urata, Tokyo (JP); Tetsuya Isaka, Chiba (JP); Taichi Shimada, Chiba (JP)

(73) Assignees: DAISAN KASEI CO., LTD, Chiba (JP); JNC CORPORATION, Tokyo (JP)

( * ) Notice: Subject to any disclaimer, the term of this patent is extended or adjusted under 35 U.S.C. 154(b) by 48 days.

(21) Appl. No.: 17/051,772

(22) PCT Filed: Jan. 31, 2019

(86) PCT No.: PCT/JP2019/003304
§ 371 (c)(1),
(2) Date: Oct. 29, 2020

(87) PCT Pub. No.: WO2019/211934
PCT Pub. Date: Nov. 7, 2019

(65) Prior Publication Data
US 2021/0230096 A1    Jul. 29, 2021

(30) Foreign Application Priority Data
May 1, 2018   (JP) .............................. JP2018-088481

(51) Int. Cl.
*C07C 69/24*   (2006.01)
*C10M 105/34*  (2006.01)
(Continued)

(52) U.S. Cl.
CPC .............. *C07C 69/24* (2013.01); *C07C 67/08* (2013.01); *C07C 69/44* (2013.01); *C07C 69/533* (2013.01);
(Continued)

(58) Field of Classification Search
CPC ......... C07C 69/24; C07C 69/44; C07C 69/82; C07C 69/533; C07C 67/08
See application file for complete search history.

(56) References Cited

U.S. PATENT DOCUMENTS 6,667,285 B1 * 12/2003 Kawahara ............ C10M 105/36
                                                          508/485
2006/0116303 A1   6/2006 Iimura et al.
2011/0039740 A1 * 2/2011 Kitching .............. C10M 169/04
                                                          508/459

FOREIGN PATENT DOCUMENTS

JP   2002146374   5/2002
JP   2003034795   2/2003
(Continued)

OTHER PUBLICATIONS

"International Search Report (Form PCT/ISA/210) of PCT/JP2019/003304," dated Mar. 26, 2019, with English translation thereof, pp. 1-4.

Primary Examiner — Yate' K Cutliff
(74) Attorney, Agent, or Firm — JCIPRNET

(57) ABSTRACT

[Problem] An ester compound having low viscosity, excellent fluidity even at low temperatures, and a high viscosity index; and a lubricating oil base oil containing said compound are provided. [Solution] The present invention provides an ester compound indicated by formula (I). Formula (I) (in formula (I), $R_1$ is a hydrocarbon group having 1 to 35 carbon atoms and at least one hydrogen in the hydrocarbon group may be independently substituted with a group indicated by formula (II)). Formula (II) (in formula (II), $R_2$ is a
(Continued)

linear alkyl having 1 to 30 carbon atoms or a branched alkyl having 3 to 30 carbon atoms.)

18 Claims, 8 Drawing Sheets

(51) Int. Cl.
  *C07C 67/08* (2006.01)
  *C07C 69/44* (2006.01)
  *C07C 69/533* (2006.01)
  *C07C 69/82* (2006.01)
  *C10M 105/36* (2006.01)
  *C10M 177/00* (2006.01)
  *C07C 69/58* (2006.01)
  *C10N 20/02* (2006.01)
  *C10N 70/00* (2006.01)
(52) U.S. Cl.
  CPC .............. *C07C 69/58* (2013.01); *C07C 69/82* (2013.01); *C10M 105/34* (2013.01); *C10M 105/36* (2013.01); *C10M 177/00* (2013.01); *C10M 2207/2815* (2013.01); *C10M 2207/2825* (2013.01); *C10M 2207/2855* (2013.01); *C10N 2020/02* (2013.01); *C10N 2070/00* (2013.01)

(56) References Cited

FOREIGN PATENT DOCUMENTS

| | | |
|---|---|---|
| JP | 2005154726 | 6/2005 |
| JP | 2006176760 | 7/2006 |
| JP | 2008037994 | 2/2008 |
| JP | 2008127491 | 6/2008 |
| JP | 2008280381 | 11/2008 |
| JP | 2009185191 | 8/2009 |
| JP | 2011518910 | 6/2011 |
| WO | 0068345 | 11/2000 |
| WO | 2017097645 | 6/2017 |
| WO | 2017116900 | 7/2017 |

\* cited by examiner

ESTER COMPOUND AND LUBRICATING OIL BASE OIL

CROSS-REFERENCE TO RELATED APPLICATION

This application is a 371 application of the international PCT application serial no. PCT/JP2019/003304, filed on Jan. 31, 2019, which claims the priority benefit of Japanese Patent Application No. 2018-088481, filed on May 1, 2018. The entirety of each of the abovementioned patent applications is hereby incorporated by reference herein and made a part of this specification.

TECHNICAL FIELD

The present invention relates to an ester compound suitable for a lubricating oil base oil, and more particularly to a carboxylic acid ester compound derived from 10-ethyl-7-tetradecanol and a lubricating oil base oil containing the same.

BACKGROUND ART

Lubricating oils are used under a wide range of conditions from low temperatures to high temperatures. In recent years, in lubricating oils used for industrial applications, various improvements have been examined for increasing efficiency thereof. For example, in order to decrease energy loss caused by viscous friction, a friction modifier is used and lowering of the viscosity of a lubricating oil is carried out. Further, there is a need for responsiveness at low temperatures, and there is a need for a product that has low viscosity at low temperatures and can contribute to saving power consumption. In order to meet such needs, lubricating oil base oils having high fluidity and a high viscosity index have been proposed.

For example, as a compound for improving low-temperature fluidity of ester, Patent Literatures 1 to 4 disclose aliphatic monocarboxylic acid ester in which a branched structure is used for the raw material alcohol.

In addition, Patent Literatures 5 and 6 disclose dibasic acid diester.

In addition, Patent Literature 7 discloses poly α-olefin. In addition, Patent Literature 8 discloses an ester base oil for lubricating oil, the ester being ester composed of alcohol, which is branched at the 6-position, and carboxylic acid, and having a total of 26 to 40 carbon atoms.

REFERENCE LIST

Patent Literature

Patent Literature 1: Japanese Patent Laid-Open No. 2002-146374
Patent Literature 2: Japanese Patent Laid-Open No. 2008-280381
Patent Literature 3: International Publication WO 2017/097645
Patent Literature 4: International Publication WO 2017/116900
Patent Literature 5: Japanese Patent Laid-Open No. 2003-34795
Patent Literature 6: Japanese Patent Laid-Open No. 2005-154726
Patent Literature 7: Japanese Patent Laid-Open No. 2006-176760
Patent Literature 8: Japanese Patent Laid-Open No. 2009-185191

SUMMARY

Technical Problem

For lubricating oil base oils, there is a demand for a base oil having a good pour point as well as suitable viscosity and viscosity index.

An objective of the present invention is to provide ester compounds having various viscosity indexes such as ester compounds having low viscosity, having excellent fluidity even at low temperatures, and having a high viscosity index, and lubricating oil base oils containing these compounds.

Solution to Problem

As a result of intensive studies, the present inventors have found that a carboxylic acid ester compound derived from 10-ethyl-7-tetradecanol has low viscosity while having high fluidity even at low temperatures and a high viscosity index. Based on this finding, the present inventors have completed the present invention.

In the present invention, there is provided an ester compound represented by Formula (I).

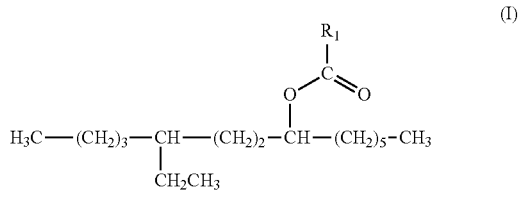

(in Formula (I), $R_1$ is a hydrocarbon group having 1 to 35 carbon atoms, in which at least one hydrogen in the hydrocarbon group may be independently substituted with a group represented by Formula (II))

(in Formula (II), $R_2$ is a linear alkyl having 1 to 30 carbon atoms or a branched alkyl having 3 to 30 carbon atoms).

In addition, in the present invention, there is provided an ester compound represented by Formula (I).

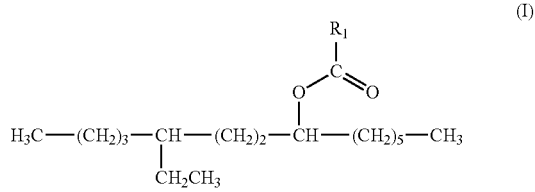

(in Formula (I), $R_1$ is a linear alkyl having 1 to 35 carbon atoms, a branched alkyl having 3 to 35 carbon atoms, or a linear alkenyl having 4 to 24 carbon atoms, in which at least one hydrogen in the alkyl and the alkenyl may be independently substituted with a group represented by Formula (II))

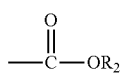

(in Formula (II), $R_2$ is a linear alkyl having 1 to 30 carbon atoms or a branched alkyl having 3 to 30 carbon atoms).

In addition, in the present invention, there is provided an ester compound represented by Formula (I).

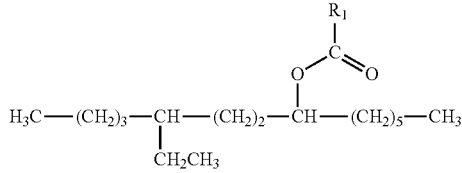

(in Formula (I), $R_1$ is phenyl, cyclohexyl, or cyclohexenyl, in which at least one hydrogen in these rings may be independently substituted with a linear alkyl having 1 to 10 carbon atoms or a group represented by Formula (II))

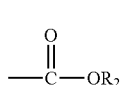

(in Formula (II), $R_2$ is a linear alkyl having 1 to 30 carbon atoms or a branched alkyl having 3 to 30 carbon atoms).

In addition, in the present invention, there is provided the above-described ester compound in which at least one hydrogen in $R_1$ is substituted with a group represented by Formula (II), and $R_2$ is a group represented by Formula (III).

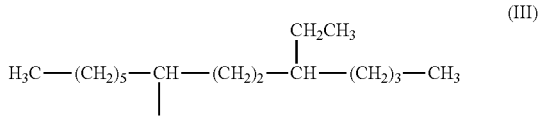

In addition, in the present invention, there is provided a lubricating oil base oil containing the above-described ester compound.

In addition, in the present invention, there is provided a method for producing the above-described ester compound, comprising a step of subjecting 10-ethyl-7-tetradecanol and carboxylic acid to esterification reaction.

Advantageous Effects of Invention

The ester compound of the present invention has low viscosity, has excellent fluidity even at low temperatures, and has a high viscosity index; and is therefore useful as a lubricating oil base oil.

DESCRIPTION OF THE EMBODIMENTS

Figure 1:
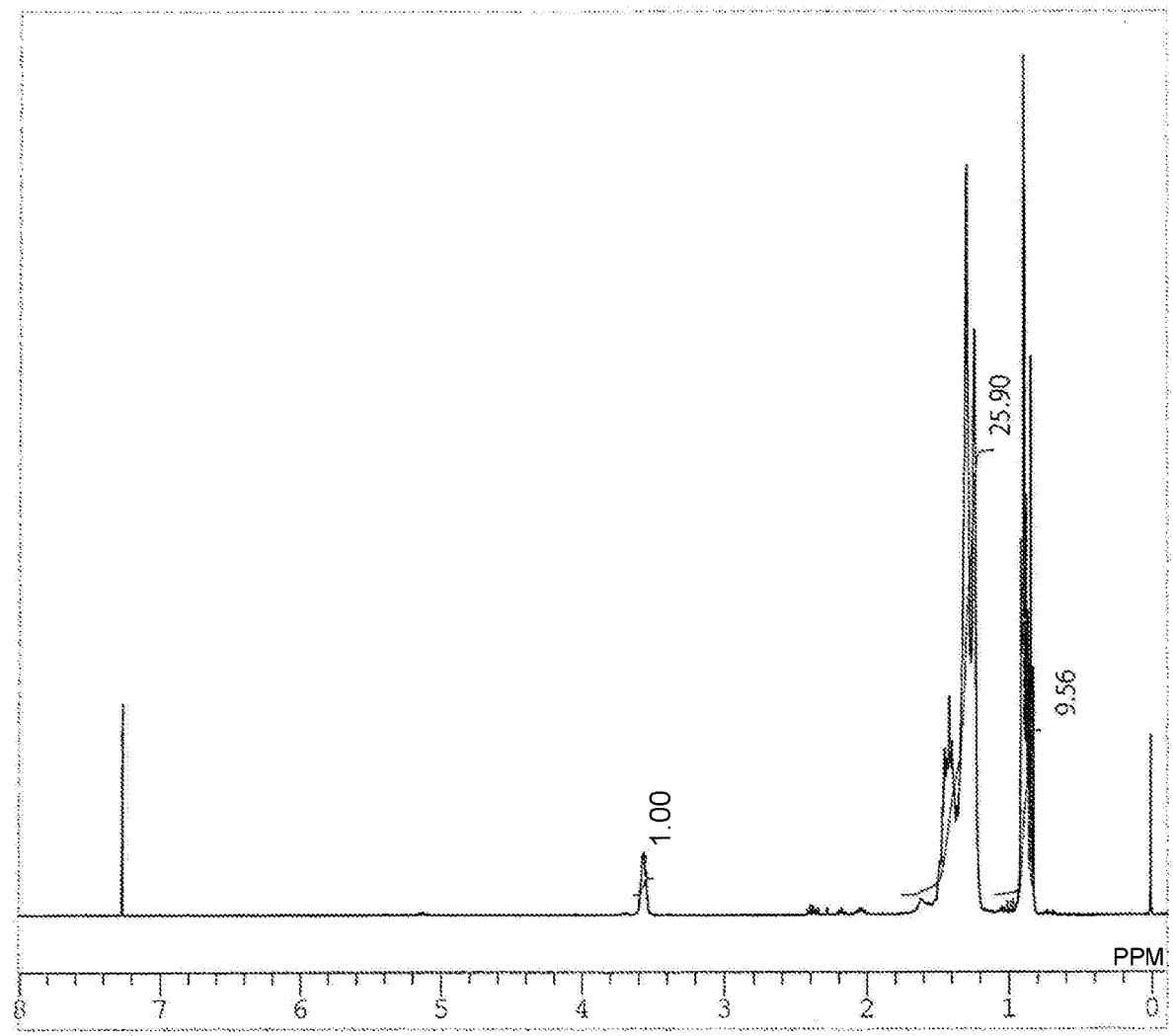
FIG. 1 illustrates a $^1$H-NMR spectrum of 10-ethyl-7-tetradecanol (3) in Example 1.

The ester compound of the present invention is represented by Formula (I).

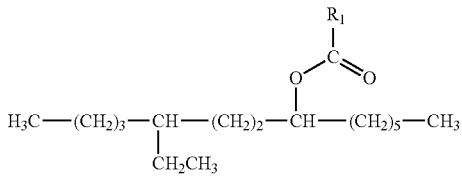

In Formula (I), $R_1$ is a hydrocarbon group having 1 to 35 carbon atoms.

The hydrocarbon group in $R_1$ may be a linear or branched, saturated or unsaturated aliphatic hydrocarbon group, an alicyclic hydrocarbon group, and an aromatic hydrocarbon group. The hydrocarbon group in $R_1$ has 1 to 35 carbon atoms, preferably 1 to 24 carbon atoms, and more preferably 1 to 18 carbon atoms.

The hydrocarbon group in $R_1$ is, for example, a linear or branched, saturated or unsaturated aliphatic hydrocarbon group, and may be a linear or branched alkyl or alkenyl. In $R_1$, the linear alkyl has 1 to 35 carbon atoms, preferably 1 to 24 carbon atoms, and more preferably 1 to 18 carbon atoms. In addition, in $R_1$, the branched alkyl has 3 to 35 carbon atoms, preferably 3 to 24 carbon atoms, and more preferably 3 to 18 carbon atoms. In $R_1$, the alkenyl has 4 to 24 carbon atoms and preferably 4 to 18 carbon atoms.

In addition, examples of the hydrocarbon group in $R_1$ include phenyl, cyclohexyl, and cyclohexenyl, with the cyclohexenyl having the double bond located at any position. In a case where $R_1$ is phenyl, cyclohexyl, or cyclohexenyl, at least one hydrogen in these rings may be independently substituted with a linear alkyl having 1 to 10 carbon atoms, or a group represented by Formula (II) as described below.

In the present invention, examples of alkyl include methyl, ethyl, isopropyl, propyl, butyl, pentyl, hexyl, heptyl, octyl, nonyl, decyl, isodecyl, dodecyl, tridecyl, tetradecyl, pentadecyl, hexadecyl, heptadecyl, octadecyl, nonadecyl, icosyl, eicosyl, henicosyl, docosyl, tricosyl, tetracosyl, pentacosyl, hexacosyl, heptacosyl, octacosyl, nonacosyl, and triacontyl. The alkyl may be branched, and the number and position of branches are not particular limited. Examples of the branched alkyl include t-butyl, 2-ethylhexyl, and 2-octyl.

In the present invention, examples of the alkenyl include ethenyl, propenyl, butenyl, pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl, icosenyl, henicosenyl, docosenyl, tricosenyl, tetracosenyl, pentacosenyl, hexacosenyl, heptacosenyl, octacosenyl, nonacosenyl, and triacontenyl. The alkenyl and other unsaturated hydrocarbon groups may be branched, and the number and position of branches are not particular limited. In addition, the alkenyl and other unsaturated hydrocarbon groups are not particularly limited in terms of the position of the unsaturated bond and isomers such as trans and cis.

In $R_1$, at least one hydrogen in the hydrocarbon group may be substituted with a group represented by Formula (II).

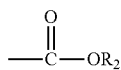
(II)

In Formula (II), $R_2$ is a linear alkyl having 1 to 30 carbon atoms or a branched alkyl having 3 to 30 carbon atoms. In $R_2$, the alkyl has preferably 10 to 20 carbon atoms and more preferably 5 to 15 carbon atoms.

In addition, for the ester compound of the present invention, in $R_1$, one hydrogen may be substituted with a group represented by Formula (II), or two or more hydrogen atoms may be substituted with a group represented by Formula (II).

In a case where two or more hydrogen atoms are substituted with the group represented by Formula (II), $R_2$ in each group may be the same or different.

As the ester compound of the present invention, for example, a compound represented by Formula (IV) may be exemplified.

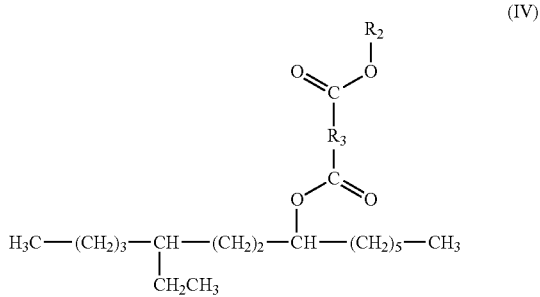
(IV)

In Formula (IV), $R_3$ is a hydrocarbon group having 1 to 35 carbon atoms.

The hydrocarbon group in $R_3$ may be a linear or branched, saturated or unsaturated aliphatic hydrocarbon group, an alicyclic hydrocarbon group, and an aromatic hydrocarbon group. The hydrocarbon group in $R_3$ has 1 to 35 carbon atoms, preferably 1 to 24 carbon atoms, and more preferably 1 to 10 carbon atoms.

In Formulas (II) and (IV), $R_2$ may be a branched alkyl having 14 to 18 carbon atoms. For example, $R_2$ includes 1-hexyl-4-ethyloctyl represented by Formula (III).

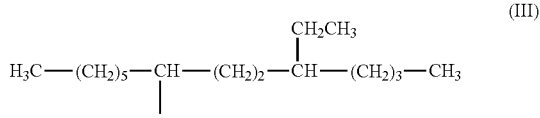
(III)

For example, as the ester compound of the present invention, a compound represented by Formula (V) may be exemplified.

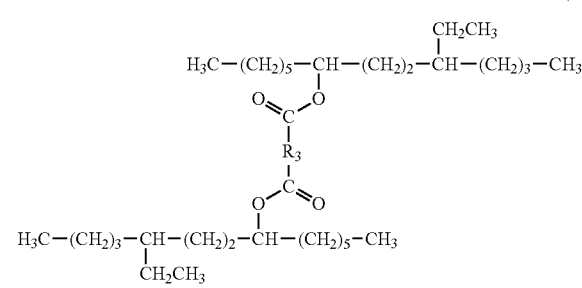
(V)

Due to the above-mentioned structure, the ester compound of the present invention has the properties of low viscosity, a low pour point (about −50° C. or lower), and high fluidity at low temperatures. In addition, the ester compound of the present invention has a sufficiently high viscosity index. Therefore, the ester compound of the present invention is useful as a lubricating oil base oil.

In addition, for the ester compound of the present invention, in $R_1$, $R_2$, and $R_3$, the number of carbon atoms and the form (linear and branched, saturated and unsaturated, and the like) of the hydrocarbon group can be appropriately changed so that the kinematic viscosity and viscosity index of the compound are adjusted to be within desired ranges while allowing a low pour point to be maintained.

The ester compound of the present invention can be produced by subjecting 10-ethyl-7-tetradecanol and carboxylic acid to esterification reaction. For example, the ester compound represented by Formula (I) can be produced by subjecting 10-ethyl-7-tetradecanol and carboxylic acid having $R_1$ to esterification reaction. In addition, the ester compound represented by Formula (V) can be produced by subjecting 10-ethyl-7-tetradecanol and dicarboxylic acid having $R_3$ to esterification reaction.

In addition, by subjecting 10-ethyl-7-tetradecanol and carboxylic acid having a plurality of three or more carboxyl groups to esterification reaction, it is possible to produce an ester compound in which all carboxyl groups in the carboxylic acid are esterified with 10-ethyl-7-tetradecanol.

In addition, the carboxylic acid to be reacted with 10-ethyl-7-tetradecanol may be a compound in which some of a plurality of carboxyl groups are esterified with another alcohol. For example, in a case of producing the compound represented by Formula (IV), the carboxylic acid used may be a compound in which one of carboxyl groups in dicarboxylic acid having $R_3$ is esterified with alcohol having $R_2$.

In addition, the ester compound of the present invention can be produced by subjecting 10-ethyl-7-tetradecanol, carboxylic acid having two or more carboxyl groups, and alcohol other than 10-ethyl-7-tetradecanol to esterification reaction. For example, the compound represented by Formula (IV) can be produced by subjecting 10-ethyl-7-tetradecanol, dicarboxylic acid having $R_3$, and alcohol having $R_2$ to esterification reaction, to obtain a mixture of ester compounds in various combinations, and then separating the compound corresponding to Formula (IV) therefrom.

The above-mentioned esterification reaction can be carried out by using any method that may be used for normal esterification reaction. In addition, the method used in the production method of the present invention as described below may be suitably used.

In addition, in the present invention, there is provided a method for producing the above-mentioned ester compound.

The production method of the present invention comprises a step of subjecting 10-ethyl-7-tetradecanol and carboxylic acid to esterification reaction.

In the step for carrying out esterification reaction in the present invention, it is possible to subject the carboxylic acid and 10-ethyl-7-tetradecanol to dehydration and condensation using any conventionally known method. For example, a method may be used in which an azeotropic agent is used in the reaction system and esterification reaction is carried out while feeding an inert gas and removing water generated by doing so. In addition, as in normal esterification reaction, a non-catalytic method and a method using a catalyst may be used.

For the step for carrying out esterification reaction in the present invention, a reaction distillation apparatus and a reactor equipped with a Dean-Stark trap, and the like may be used.

For the step of carrying out esterification reaction in the present invention, in order to remove water out of the reaction system for water to be removed out of the reaction system, an organic solvent that is inert in the esterification reaction and forms an azeotrope with water may be used as the azeotropic agent. As such an azeotropic agent, for example, toluene, ethyl benzene, benzene, cyclohexane, and the like may be used. In addition, as a method for removing water in the esterification reaction, it is also possible to use a method in which an inert gas is fed to a reactor and water generated by dosing so is removed. For example, nitrogen gas or the like may be used as the inert gas.

As the catalyst used in the step for carrying out esterification reaction in the present invention, p-toluene sulfonic acid, an ion exchange resin containing a sulfonic group, mineral acid (inorganic acid) such as sulfuric acid and phosphoric acid, titanium tetraisopropoxide, titanium tetrabutoxide, tin 2-ethylhexanoate, tin oxide, tin chloride, and 3-boron trifluoride ether complex may be exemplified. In particular, in a case where highly reactive carboxylic acid is used, it is possible to carry out the reaction without using any catalyst.

10-Ethyl-7-tetradecanol may be obtained, for example, by the Guerbet reaction of 2-ethylhexanol with 2-octanol. Specifically, 10-ethyl-7-tetradecanol may be produced by subjecting 2-ethylhexanol and 2-octanol to thermal condensation in the presence of alkali metal hydroxide and a dehydrogenation catalyst.

2-Ethylhexanol may be produced at a large scale by carrying out aldol condensation and hydrogenation reaction of n-butyraldehyde that is obtained by oxo reaction using propylene. 2-Octanol may be obtained by subjecting ricinoleic acid in castor oil to decomposition, and is available at a relatively low cost from the oil chemical industry.

As the alkali metal hydroxide, sodium hydroxide, potassium hydroxide, lithium hydroxide, and the like may be used. As the dehydrogenation catalyst, a metal element may be used, which is usually used in the Guerbet reaction, such as zinc, zinc oxide, organic zinc, nickel, chromium, copper, platinum, palladium, ruthenium, and rhodium. In addition, as the dehydrogenation catalyst, an immobilized catalyst may be used, in which the above-mentioned metal element is supported on a carrier. As the carrier, alumina, activated carbon, or the like may be used.

The thermal condensation reaction may be carried out, for example, at 180° C. to 230° C. under a normal pressure condition. In a case where the temperature is 180° C. or higher, an increased reaction rate can be achieved. In addition, in a case where the temperature is 230° C. or lower, a decrease in the amount produced of high-boiling-point compounds other than the desired alcohol can be achieved. In addition, the thermal condensation reaction may be carried out under pressurized conditions in order to raise the reaction temperature so that the reaction rate is increased.

10-Ethyl-7-tetradecanol may be purified by distillation using conventional simple distillation apparatus and rectification column. Further, the purity thereof may be increased by performing treatments such as hydrogenation, adsorbent, extraction, washing, and column chromatography.

The compound of Formula (I) can be produced according to the general reaction as outlined below. Some of the synthetic procedures for bringing about the compound of Formula (I) are described below.

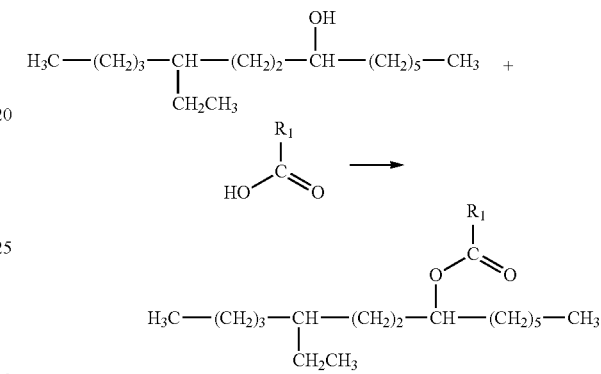

The compound of Formula (I) can be produced by subjecting 10-ethyl-7-tetradecanol and carboxylic acid having desired $R_1$ to esterification reaction. 10-ethyl-7-tetradecanol and the carboxylic acid having desired $R_1$ are added to a four-necked flask, equipped with a thermometer, a stirrer, a nitrogen inlet tube, and a Dean-Stark trap with a Dimroth reflux condenser, and heated at 180° C. to 230° C., for example, 200° C. to 220° C. At this time, heating may be performed while feeding nitrogen gas. In addition, at the time of heating, heating may be performed with addition of a reaction catalyst such as tetraisopropyl titanate. The water generated by the reaction is removed from the Dean-Stark trap. Heating is performed, for example, for 10 to 20 hours until the reaction is completed, and then cooling is performed. Next, washing was performed with 3 wt % $Na_2CO_3$ aqueous solution, and then washing is performed with water. Next, low boiling components are distilled off at 200° C. under a vacuum, to obtain a desired ester compound. Alternatively, after heating, unreacted 10-ethyl-7-tetradecanol and unreacted carboxylic acid may be removed. For example, after heating, cooling is performed down to 70° C., water is added, and stirring is performed for 30 minutes. Next, the reaction solution is transferred to a simple distillation apparatus, and the unreacted 10-ethyl-7-tetradecanol and carboxylic acid are collected as fractions over 4 hours at a liquid temperature of approximately 230° C. and under vacuum of approximately 6 torr (800 Pa) in the apparatus. Cooling is performed at 70° C., and then stirring is performed for 5 minutes in 20 wt % NaOH aqueous solution. Next, the washing water and the catalyst residue are removed by liquid separation. Washing with 20 wt % NaOH aqueous solution is performed 3 times, to obtain crude ester. Washing with water is performed at 70° C., to decrease the sodium component remaining in the crude ester. Next, water is distilled off at 140° C. under vacuum of 6 torr (800 Pa). Subsequently, activated carbon is added for the purpose of removing residual carboxylic acid and catalyst residue, and stirring is performed at 80° C. for 2 hours. Then, suction filtration is performed to obtain a desired ester compound.

In addition, the synthetic procedure for bringing about the compound of Formula (V) is described below.

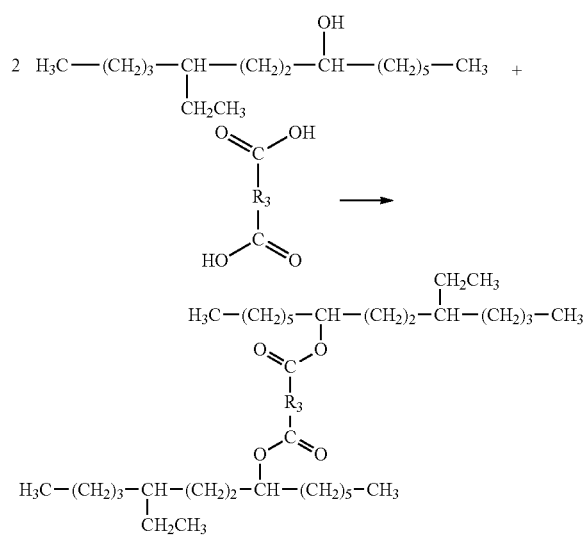

The compound of Formula (V) can be produced by subjecting 10-ethyl-7-tetradecanol and dicarboxylic acid having desired $R_3$ to esterification reaction. 10-ethyl-7-tetradecanol and carboxylic acid having desired $R_3$ are added to a four-necked flask, equipped with a thermometer, a stirrer, a nitrogen inlet tube, and a Dean-Stark trap with a Dimroth reflux condenser, and heated at 180° C. to 230° C., for example, 200° C. to 220° C. At this time, heating may be performed while feeding nitrogen gas. In addition, at the time of heating, heating may be performed with addition of a reaction catalyst such as tetraisopropyl titanate. The water generated by the reaction is removed from the Dean-Stark trap. Heating is performed, for example, for 10 to 20 hours until the reaction is completed, and then cooling is performed. Next, washing was performed with 3 wt % $Na_2CO_3$ aqueous solution, and then washing is performed with water. Next, low boiling components are distilled off at 200° C. under vacuum, to obtain a desired ester compound. Alternatively, after heating, unreacted 10-ethyl-7-tetradecanol and unreacted carboxylic acid may be removed. For example, after heating, cooling is performed down to 70° C., water is added, and stirring is performed for 30 minutes. Next, the reaction solution is transferred to a simple distillation apparatus, and the unreacted 10-ethyl-7-tetradecanol and carboxylic acid are collected as fractions over 4 hours at liquid temperature of approximately 230° C. and under vacuum of approximately 6 torr (800 Pa) in the apparatus. Cooling is performed at 70° C., and then stirring is performed for 5 minutes in 20 wt % NaOH aqueous solution. Next, the washing water and the catalyst residue are removed by liquid separation. Washing is performed 3 times with 20 wt % NaOH aqueous solution, to obtain crude ester. Washing is performed at 70° C. with water, to decrease the sodium component remaining in the crude ester. Next, water is distilled off at 140° C. under vacuum of 6 torr (800 Pa). Subsequently, activated carbon is added for the purpose of removing residual carboxylic acid and catalyst residue, and stirring is performed at 80° C. for 2 hours. Then, suction filtration is performed to obtain a desired ester compound.

By using, as a starting material, another alcohol in addition to 10-ethyl-7-tetradecanol in the above reaction procedure, ester compounds can be obtained in which each dicarboxylic acid is condensed with different alcohol. For example, the compound represented by Formula (IV) can be produced by subjecting 10-ethyl-7-tetradecanol, dicarboxylic acid having desired $R_3$, and alcohol having desired $R_2$ are subjected to esterification reaction using the above procedure, to obtain a mixture of ester compounds in various combinations, and then separating the compound corresponding to Formula (IV) therefrom.

In the method for producing an ester compound of the present invention, carboxylic acid having 2 to 36 carbon atoms, for example, 2 to 25 carbon atoms may be used as the carboxylic acid. The carboxylic acid may be monocarboxylic acid or may be carboxylic acid having a plurality of carboxyl groups such as dicarboxylic acid and tricarboxylic acid. The carboxylic acid may be linear or branched. In addition, the carboxylic acid may be saturated or unsaturated, aliphatic, alicyclic, or aromatic carboxylic acid.

The aliphatic carboxylic acid may be linear or branched. As the linear aliphatic carboxylic acid, for example, ethanoic acid, propanoic acid, butanoic acid, pentanoic acid, hexanoic acid, heptanoic acid, octanoic acid, nonanoic acid, decanoic acid, undecanoic acid, dodecanoic acid, tridecanoic acid, tetradecanoic acid, pentadecanoic acid, hexadecanoic acid, heptadecanoic acid, octadecanoic acid, nonadecanoic acid, icosanoic acid, eicosanoic acid, henicosanoic acid, docosanoic acid, tricosanoic acid, tetracosanoic acid, and the like may be used.

As the branched aliphatic carboxylic acid, for example, 2-methylpropanoic acid, 2-methylbutanoic acid, 2,2-dimethylpropionic acid, isohexanoic acid, isoheptanoic acid, neoheptanoic acid, 2-ethylbutanoic acid, isooctanoic acid, neooctanoic acid, 5,7,7-trimethyl-2-(1,3,3-trimethylbutyl) octanoic acid, 3,5,5-trimethylhexanoic acid, neononanoic acid, isononanoic acid, 2-propylheptanoic acid, neodecanoic acid, isodecanoic acid, 2-butyloctanoic acid, 2-pentylnonanoic acid, 2-hexyldecanoic acid, 2-heptylundecanoic acid, 2-octyldodecanoic acid, 2-nonyltridecanoic acid, 2-decyltetradecanoic acid, 2-undecylpentadecanoic acid, and the like may be used.

As the branched aliphatic carboxylic acid, fatty acid of natural origin, for example, fatty acid whose branch position is not at the α-position may be used. For example, mixed carboxylic acid (for example, trade name: PRISORINE 3505, manufactured by Uniqema; Emery 871, manufactured by Emery Oleochemicals) may be used, which is a byproduct obtained at the time of producing polymerized fatty acid using, as a raw material, oleic acid or linoleic acid, or the like.

As the unsaturated carboxylic acid, for example, acrylic acid, crotonic acid, isocrotonic acid, 3-butenoic acid, methacrylic acid, angelic acid, tiglic acid, 4-pentenoic acid, 2-ethyl-2-butenoic acid, 10-undecenoic acid, cis-9-tetradecenoic acid, cis-9-hexadecenoic acid, oleic acid, trans-9-octadecenoic acid, cis-13-dococenoic acid, trans-13-docosenoic acid, 21-triacontenoic acid, 2,4-hexadienoic acid, 9,12-octadecadienoic acid, 9,11,13-octadecatrienoic acid, 9,12,15-octadecatrienoic acid, 5,8,11,14-eicosatetraenoic acid, and the like may be used.

Examples of the aromatic carboxylic acid include monocarboxylic acid such as benzoic acid, p-methylbenzoic acid, m-methylbenzoic acid, and cinnamic acid. In addition, dicarboxylic acid such as phthalic acid, isophthalic acid, and terephthalic acid, and tricarboxylic acid such as trimellitic acid and trimesic acid may be exemplified.

In addition, instead of the aromatic carboxylic acid, corresponding acid chloride that is highly reactive in esterification may be used. For example, monocarboxylic chloride such as benzoyl chloride, naphthoic acid chloride, p-methylbenzoic acid chloride, and m-methylbenzoic acid chloride may be exemplified. In addition, dicarboxylic acid chloride such as phthalic acid chloride, isophthalic acid chloride, and terephthalic acid chloride, and tricarboxylic chloride such as trimellitic acid chloride and trimesic acid chloride may be exemplified.

As the dicarboxylic acid, for example, aliphatic dicarboxylic acid such as ethanedioic acid, propanedioic acid, butanedioic acid, pentanedioic acid, hexanedioic acid, heptanedioic acid, octanedioic acid, nonanedioic acid, decanedioic acid, undecanedioic acid, dodecanedioic acid, butyloctanedioic acid, tridecanedioic acid, tetradecanedioic acid, pentadecanedioic acid, hexadecanedioic acid, heptadecanedioic acid, octadecanedioic acid, nonadecanedioic acid, icosanedioic acid, eicosanedioic acid, isoeicosanedioic acid, eicosadiendioic acid, henicosanedioic acid, docosanedioic acid, isodocosanedioic acid, isodocosadienedioic acid, tricosanedioic acid, and tetracosanedioic acid may be used. These include all their isomers. In addition, the dicarboxylic acid may be branched, for example, 2,4-diethylglutaric acid, octenyl succinic acid, and 3-dodecenyl succinic anhydride may be exemplified. In addition, as the cyclic dicarboxylic acid, 1,4-cyclohexanedicarboxylic acid, 1,2,3,6-tetrahydrophthalic anhydride, hexahydrophthalic anhydride, 4-methylhexahydrophthalic anhydride, dimeric acid mainly composed of dicarboxylic acid having 36 carbon atoms which has a branched structure and/or an alicyclic ring structure generated by dimerization of unsaturated fatty acid having 18 carbon atoms, and the like may be exemplified.

As the tricarboxylic acid, for example, alicyclic tricarboxylic acid such as aconitic acid and cyclohexanetricarboxylic acid, and the like may be used.

In addition, in the present invention, carboxylic acid having four or more carboxyl groups may be used as the carboxylic acid. Examples of such carboxylic acid include 1,2,3,4-butanetetracarboxylic acid, 1,2,3,4-cyclobutanetetracarboxylic acid, and the like.

In addition, as the carboxylic acid including unsaturated carboxylic acid and aliphatic carboxylic acid, animal and vegetable fatty acid may be used, such as beef fatty acid, coconut oil fatty acid, and fish oil fatty acid and tall oil fatty acid may be used.

In addition, in the present invention, there is provided lubricating oil base oil containing the ester compound of the present invention. In the lubricating oil base oil of the present invention, the ester compound of the present invention can be contained as a main component. In the lubricating oil base oil of the present invention, the ester compound of the present invention may be contained singly or two or more thereof may be contained in combination.

The lubricating oil base oil of the present invention may have a viscosity index of, for example, 50 or higher, 70 or higher, and preferably 100 or higher. The viscosity index is a value measured in accordance with the method specified in JIS K 2269.

The lubricating oil base oil of the present invention may have a pour point of −50° C. or lower. The pour point is a value measured in accordance with the method specified in JIS K 2269.

For the lubricating oil base oil of the present invention, the kinematic viscosity thereof may have any respective predetermined values at respective temperatures of 40° C. and 100° C. For example, the kinematic viscosity may be 1 to 100 mm$^2$/s at 40° C. and 1 to 100 mm$^2$/s at 100° C. The kinematic viscosity is a value measured by a Ubbelohde viscometer under respective temperature conditions.

The lubricating oil base oil of the present invention may further contain any component other than the ester compound of the present invention. For example, the lubricating oil base oil of the present invention may contain another base oil such as mineral oil, poly-α-olefin, polybutene, alkylbenzene, alkylnaphthalene, animal and vegetable oil, organic acid ester other than the ester compound of the present invention, polyalkylene glycol, polyvinyl ether, polyphenyl ether, and alkylphenyl ether.

The lubricating oil base oil of the present invention can be contained in a lubricating oil composition. In addition to the lubricating oil base oil, the lubricating oil composition may further contain, if necessary, additives such as an antioxidant, a hydrolysis inhibitor, an oily agent, a detergent-dispersant, a defoamer, an anti-rust agent, an anti-emulsifier, a pour point-lowering agent, and a viscosity index-improving agent.

EXAMPLES

Hereinafter, the effects of the present invention will be specifically described by way of examples. However, the present invention is not limited thereto. The measuring apparatuses used in the present examples are as shown below.

The proton nuclear magnetic resonance spectrum was measured with an apparatus (JNM-ECZ400S: 400 MHz) manufactured by JEOL Ltd. using deuterated chloroform as a solvent and tetramethylsilane as an internal standard. GC-MS: GC-MS TQ8040NC, manufactured by Shimadzu Corporation; Column: Agilent J&W GC column DB-5 ms 30 m×0.25 μm film thickness. For detection, the CI method (with methane as reagent gas) was used.

The kinematic viscosity was a value measured under each temperature condition by an Ubbelohde viscometer, and the viscosity index was determined in accordance with the method specified in JIS K 2269. The pour point was measured in accordance with the method specified in JIS K 2269.

Example 1

Synthesis of 10-ethyl-7-tetradecanol (3) (Synthesis of Alcohol)

Figure 2:
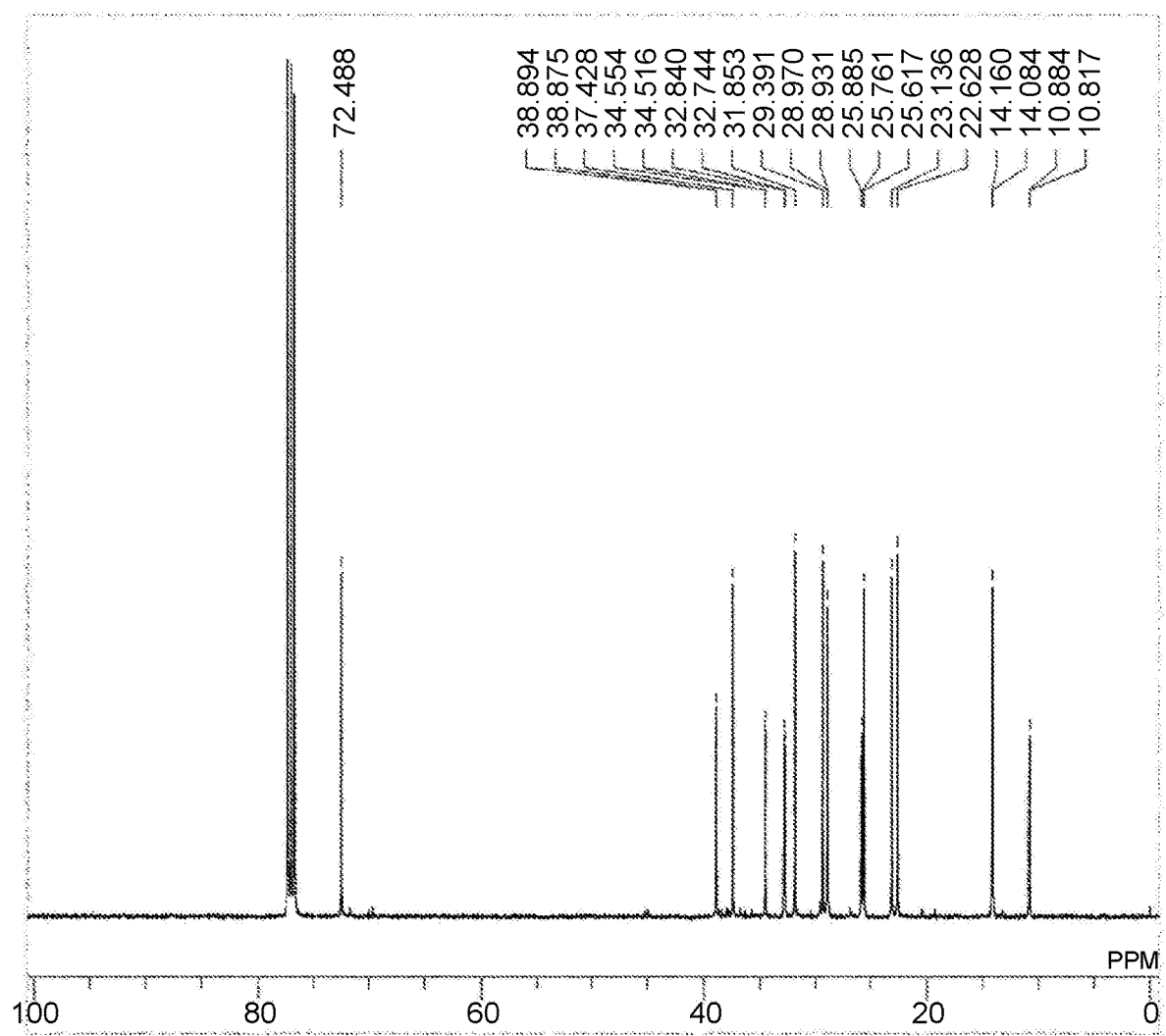
FIG. 2 illustrates a $^{13}$C-NMR spectrum of 10-ethyl-7-tetradecanol (3) in Example 1.

A 500 mL four-necked flask was equipped with a thermometer, a stirrer, a dropping funnel, and a Dean-Stark trap with a Dimroth reflux condenser. To the flask were added 130.2 g (1.00 mol) of 2-ethylhexanol (octanol, manufactured by JNC Corporation), 19.6 g (0.15 mol) of 2-octanol (special grade reagent, manufactured by Wako Pure Chemical Industries, Ltd.), 0.12 g (0.2 mmol) of zinc stearate (special grade reagent, manufactured by Wako Pure Chemical Industries, Ltd.), and 4.15 g of 85 wt % potassium hydroxide (special grade reagent, manufactured by Wako Pure Chemical Industries, Ltd.), and the contents were refluxed. The water generated by the reaction was removed from the Dean-Stark trap. 14 g to 15 g of 2-octanol was fed in portions with the dropping funnel so that the temperature inside the reactor did not fall below 188° C. The total amount of 2-octanol used was 93.0 g (0.71 mol). At 20 hours of reaction, the temperature inside the reactor reached 200° C. The reactivity at this time was 69% based on 2-ethylhexanol. The selectivity was 80%. The reaction product was washed with water, and then distilled under reduced pressure using a 20-stage glass Oldershaw. A fraction having a boiling point of 120° C. to 130° C. (2.3 torr; 310 Pa) was collected. The purity by gas chromatography was 98.5%. For this compound, the $^1$H-NMR spectrum is illustrated in FIG. 1, and the $^{13}$C-NMR spectrum is illustrated in FIG. 2.

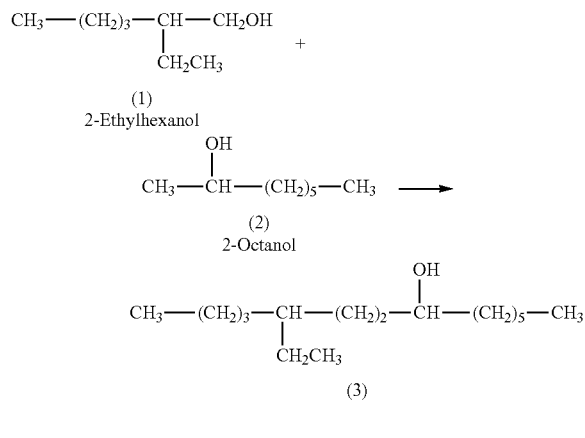

Synthesis of 1-hexyl-4-ethyloctyl Decanoate (4)

Figure 3:
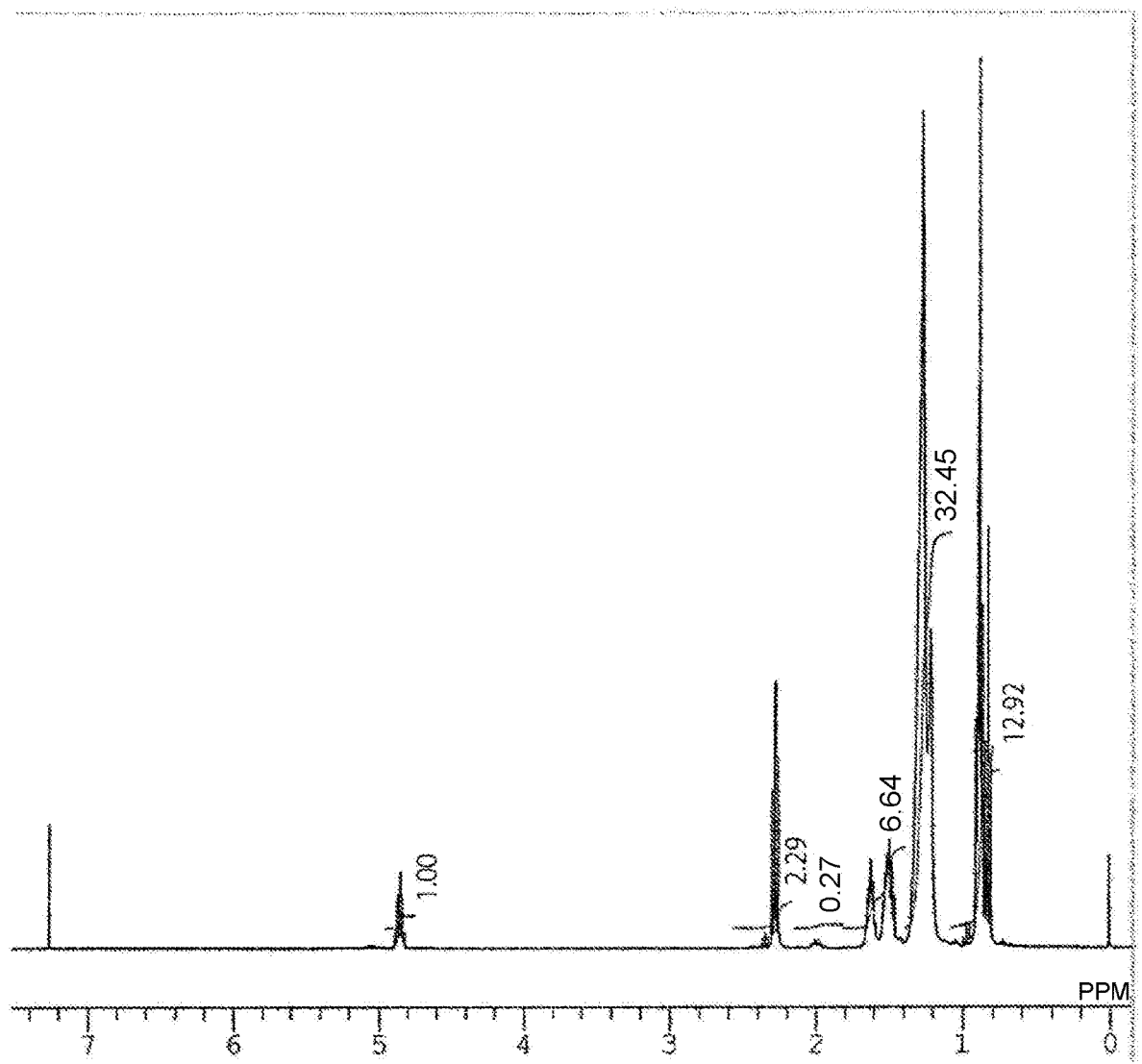
FIG. 3 illustrates a $^1$H-NMR spectrum of 1-hexyl-4-ethyloctyl decanoate (4) in Example 1.

A 500 mL four-necked flask was equipped with a thermometer, a stirrer, a nitrogen introduction tube, and a Dean-Stark trap with a Dimroth reflux condenser. To the flask were added 120.0 g (697 mmol) of n-decanoic acid (special grade reagent, manufactured by Wako Pure Chemical Industries, Ltd.) and 140.0 g (577 mmol) of 10-ethyl-7-tetradecanol, and heating was performed at 200° C. to 210° C. while feeding nitrogen gas. The water generated by the reaction was removed from the Dean-Stark trap. The reaction was carried out for 12 hours. Washing was performed with 3 wt % Na$_2$CO$_3$ aqueous solution. Then, washing was performed with water and low boiling components were distilled off at 200° C. under vacuum. Activated carbon (SHIRASAGI C, manufactured by Osaka Gas Chemicals Co., Ltd.) was added for the purpose of removing colored substances, and stirring was performed at 80° C. for 2 hours. Then, suction filtering was performed to obtain 169.0 g (yield: 73%) of compound (4). For this compound, the $^1$H-NMR spectrum is illustrated in FIG. 3.

CH$_3$—(CH$_2$)$_8$—C(=O)OH
n-Decanoic acid

CH$_3$—(CH$_2$)$_3$—CH(CH$_2$CH$_3$)—(CH$_2$)$_2$—CH(O—C(=O)—(CH$_2$)$_8$—CH$_3$)—(CH$_2$)$_5$—CH$_3$
(4)

Example 2

Synthesis of 1-hexyl-4-ethyloctyl Dodecanoate (5)

Using the same apparatus as for the esterification reaction in Example 1, 83.0 g (414 mmol) of n-dodecanoic acid (first grade reagent, manufactured by Wako Pure Chemical Industries, Ltd.) and 100.0 g (413 mmol) of 10-ethyl-7-tetradecanol were added thereto, and heating was performed at 200° C. to 210° C. while feeding nitrogen gas. The water generated by the reaction was removed from the Dean-Stark trap. The reaction was carried out for 21 hours. Washing was performed with 3 wt % Na$_2$CO$_3$ aqueous solution. Then, washing was performed with water and low boiling components were distilled off at 200° C. under vacuum. Treatment with activated carbon was performed to obtain 109.0 g (yield: 62%) of compound (5).

CH$_3$—(CH$_2$)$_{10}$—C(=O)OH + (3) →
n-Dodecanoic acid

CH$_3$—(CH$_2$)$_3$—CH(CH$_2$CH$_3$)—(CH$_2$)$_2$—CH(O—C(=O)—(CH$_2$)$_{10}$—CH$_3$)—(CH$_2$)$_5$—CH$_3$
(5)

Example 3

Synthesis of 1-hexyl-4-ethyloctyl Tetradecanoate (6)

Using the same apparatus as for the esterification reaction in Example 1, 189.0 g (828 mmol) of n-tetradecanoic acid (special grade reagent, manufactured by Wako Pure Chemical Industries, Ltd.) and 162.0 g (668 mmol) of 10-ethyl-7-tetradecanol were added thereto, and heating was performed at 200° C. to 210° C. while feeding nitrogen gas. The water generated by the reaction was removed from the Dean-Stark trap. The reaction was carried out for 22 hours. Washing was performed with 3 wt % Na$_2$CO$_3$ aqueous solution. Then, washing was performed with water and low boiling components were distilled off at 210° C. under vacuum. Treatment with activated carbon was performed to obtain 218.0 g (yield: 72%) of compound (6).

CH$_3$—(CH$_2$)$_{12}$—C(=O)OH + (3) →
n-Tetradecanoic acid

-continued

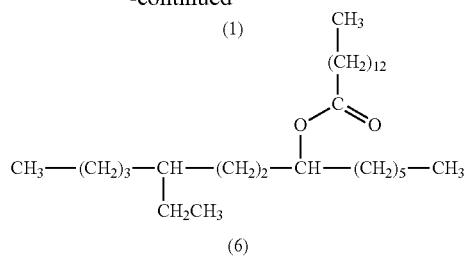

(1)

(6)

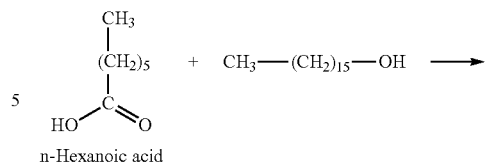

n-Hexanoic acid (8)

Example 4

Synthesis of 1-hexyl-4-ethyloctyl Hexanoate (7)

Using the same apparatus as for the esterification reaction in Example 1, 80.1 g (690 mmol) of n-hexanoic acid (HS, manufactured by JNC Corporation) and 140.0 g (577 mmol) of 10-ethyl-7-tetradecanol were added thereto, and heating was performed at 200° C. to 210° C. while feeding nitrogen gas. The water generated by the reaction was removed from the Dean-Stark trap. The reaction was carried out for 20 hours. Washing was performed with 3 wt % $Na_2CO_3$ aqueous solution. Then, washing was performed with water and low boiling components were distilled off at 200° C. under vacuum. Treatment with activated carbon was performed to obtain 154.0 g (yield: 78%) of compound (7).

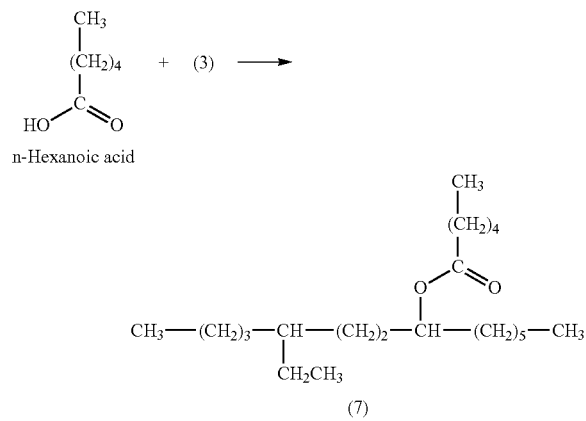

n-Hexanoic acid (7)

Comparative Example 1

Synthesis of 1-hexadecyl n-Hexanoate (8)

Using the same apparatus as for the esterification reaction in Example 1, 80.0 g (694 mmol) of n-hexanoic acid (HS, manufactured by JNC Corporation) and 140.0 g (577 mmol) of n-hexadecanol (first grade reagent, manufactured by Wako Pure Chemical Industries, Ltd.) were added thereto, and heating was performed at 200° C. to 210° C. The water generated by the reaction was removed from the Dean-Stark trap. The reaction was carried out for 20 hours. Washing was performed with 3 wt % $Na_2CO_3$ aqueous solution. Then, washing was performed with water and low boiling components were distilled off at 200° C. under vacuum. Treatment with activated carbon was performed to obtain 192.0 g (yield: 97%) of compound (8).

Example 5

Synthesis of 1-hexyl-4-ethyloctyl 2-hexyldecanoate (9)

Figure 4:
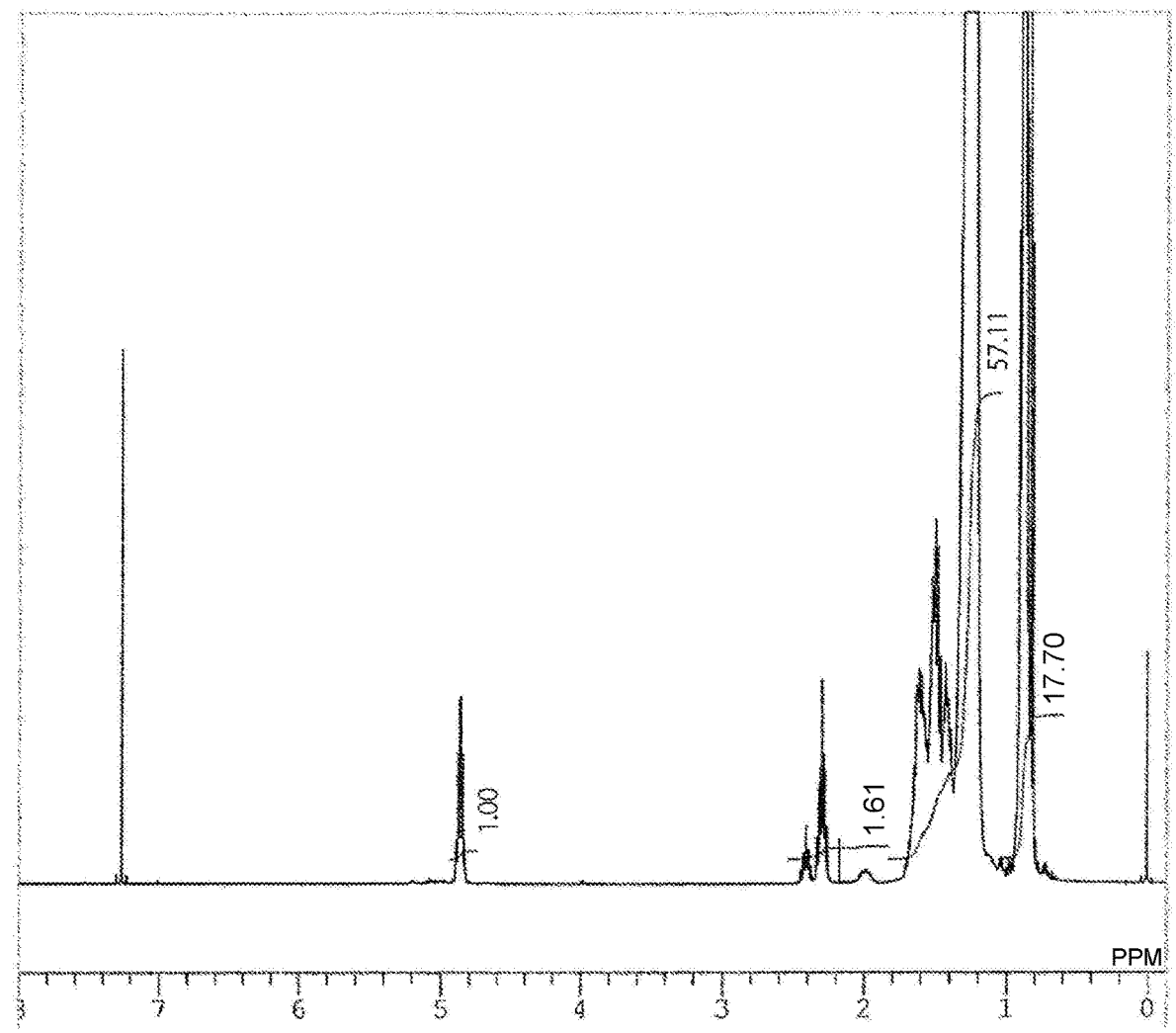
FIG. 4 illustrates a $^1$H-NMR spectrum of 1-hexyl-4-ethyloctyl 2-hexyldecanoate (9) in Example 5.

Using the same apparatus as for the esterification reaction in Example 1, 127.0 g (495 mmol) of 2-hexyldecanoic acid (manufactured by Daisan Kasei Co., Ltd.), 134.0 g (552 mmol) of 10-ethyl-7-tetradecanol, and 150 mg of tetraisopropyl titanate (ORGATIX TA-8, manufactured by Matsumoto Fine Chemical Co., Ltd.) were added thereto, and heating was performed at 200° C. to 210° C. The water generated by the reaction was removed from the Dean-Stark trap. The reaction was carried out for 14 hours. Cooling was performed down to 70° C. Then, 3 g of water was added, and stirring was performed for 30 minutes. The reaction solution was transferred to a simple distillation apparatus, and the unreacted compound (3) and 2-hexyldecanoic acid were collected as fractions over 4 hours at a liquid temperature of approximately 230° C. and under a vacuum of approximately 6 torr (800 Pa) in the apparatus. Cooling was performed at 70° C., and then stirring was performed for 5 minutes in 20 wt % NaOH aqueous solution. The washing water and the catalyst residue were removed by liquid separation. Washing with 20 wt % NaOH aqueous solution was performed 3 times, to obtain crude ester. Washing with water was performed at 70° C., to decrease the sodium component remaining in the crude ester. Next, water was distilled off at 140° C. under vacuum of 6 torr (800 Pa). Subsequently, activated carbon (SHIRASAGI C) was added for the purpose of removing residual carboxylic acid and catalyst residue, and stirring was performed at 80° C. for 2 hours. Then, suction filtration was performed to obtain 189 g (yield: 75%) of compound (9). For this compound, the $^1$H-NMR chart is illustrated in FIG. 4. GC-MS 479 ($M^+$-$H_1$).

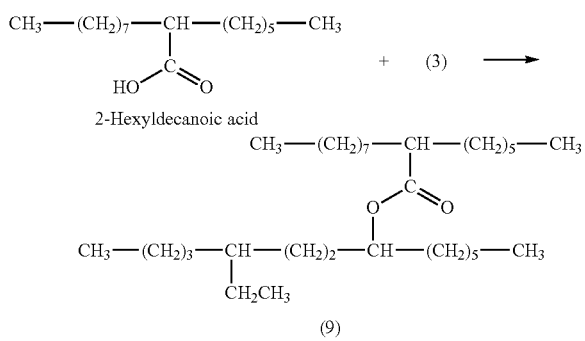

2-Hexyldecanoic acid (9)

Example 6

Synthesis of 1-hexyl-4-ethyloctyl 2-ethylhexanoate (10)

Using the same apparatus as for the esterification reaction in Example 1, 108.0 g (749 mmol) of 2-ethylhexanoic acid (2-EHS, manufactured by JNC Corporation) and 140.0 g (577 mmol) of 10-ethyl-7-tetradecanol were added thereto, and heating was performed at 200° C. to 220° C. The water generated by the reaction was removed from the Dean-Stark trap. The reaction was carried out for 23 hours. Treatment was performed in the same manner as in Example 5, to obtain 165.0 g (yield: 78%) of compound (10).

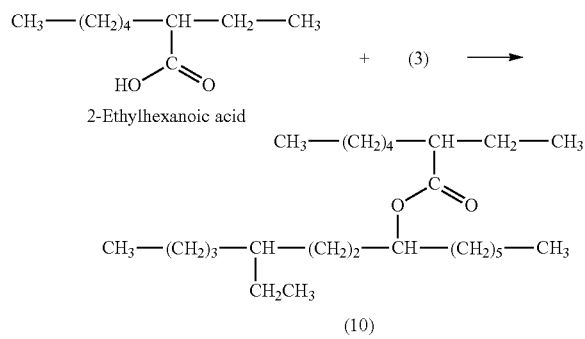

Example 7

Synthesis of 1-hexyl-4-ethyloctyl Isostearate (11)

Figure 5:
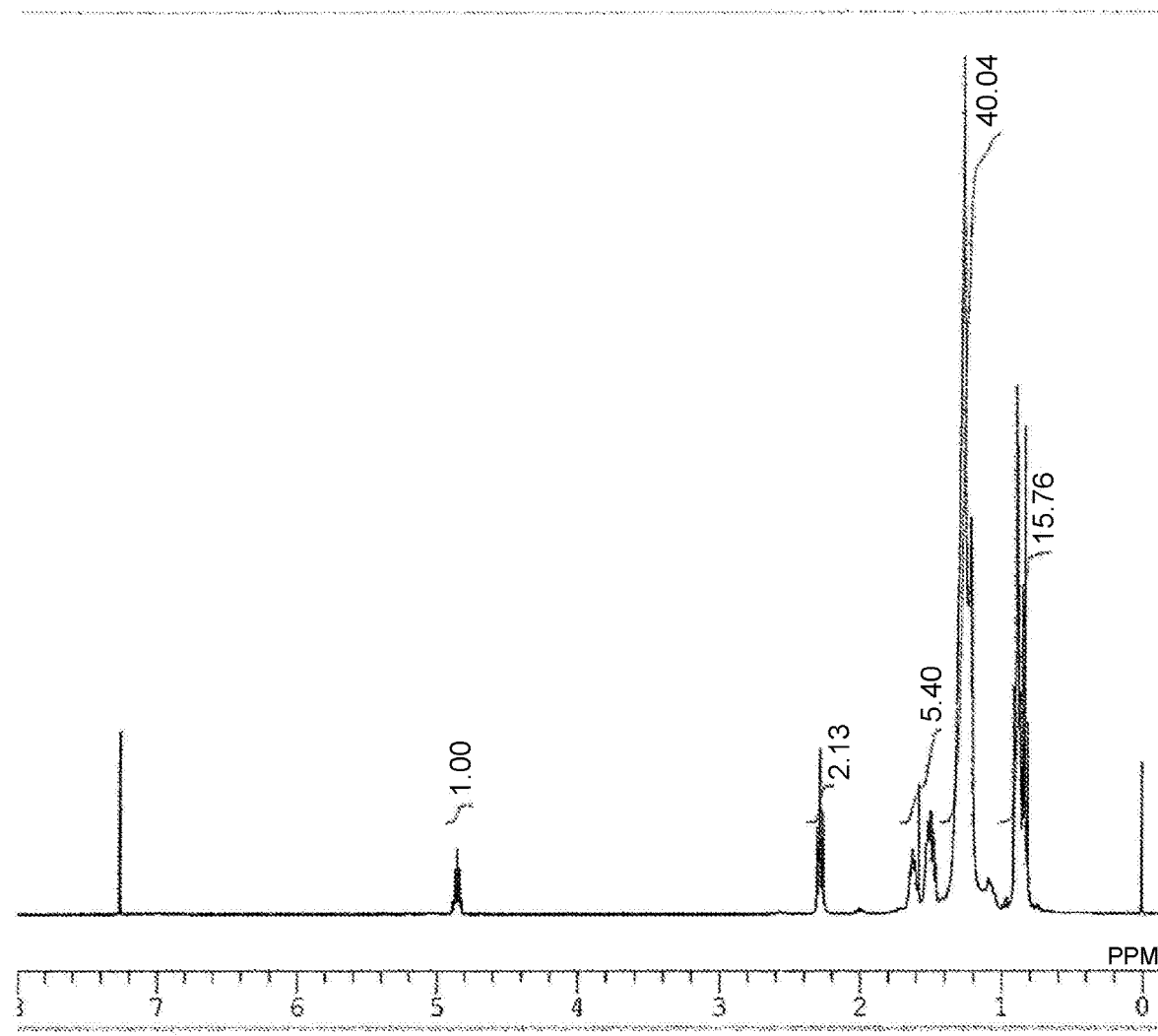
FIG. 5 illustrates a $^1$H-NMR spectrum of 1-hexyl-4-ethyloctyl isostearate (11) in Example 7.

Using the same apparatus as for the esterification reaction in Example 1, 118.0 g of isostearic acid (PRISORINE 3505-LQ, manufactured by CRODA) and 220.0 g (907 mmol) of 10-ethyl-7-tetradecanol were heated at 210° C. to 220° C. The water generated by the reaction was removed from the Dean-Stark trap. The reaction was carried out for 35 hours. Treatment was performed in the same manner as in Example 5, to obtain 182.0 g of compound (11). For this compound, the $^1$H-NMR spectrum is illustrated in FIG. 5.

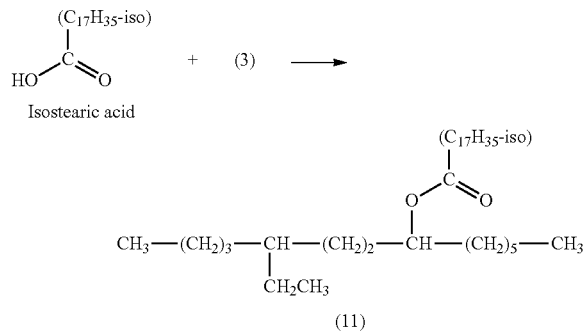

Example 8

Synthesis of 1-hexyl-4-ethyloctyl Oleate (12)

Figure 6:
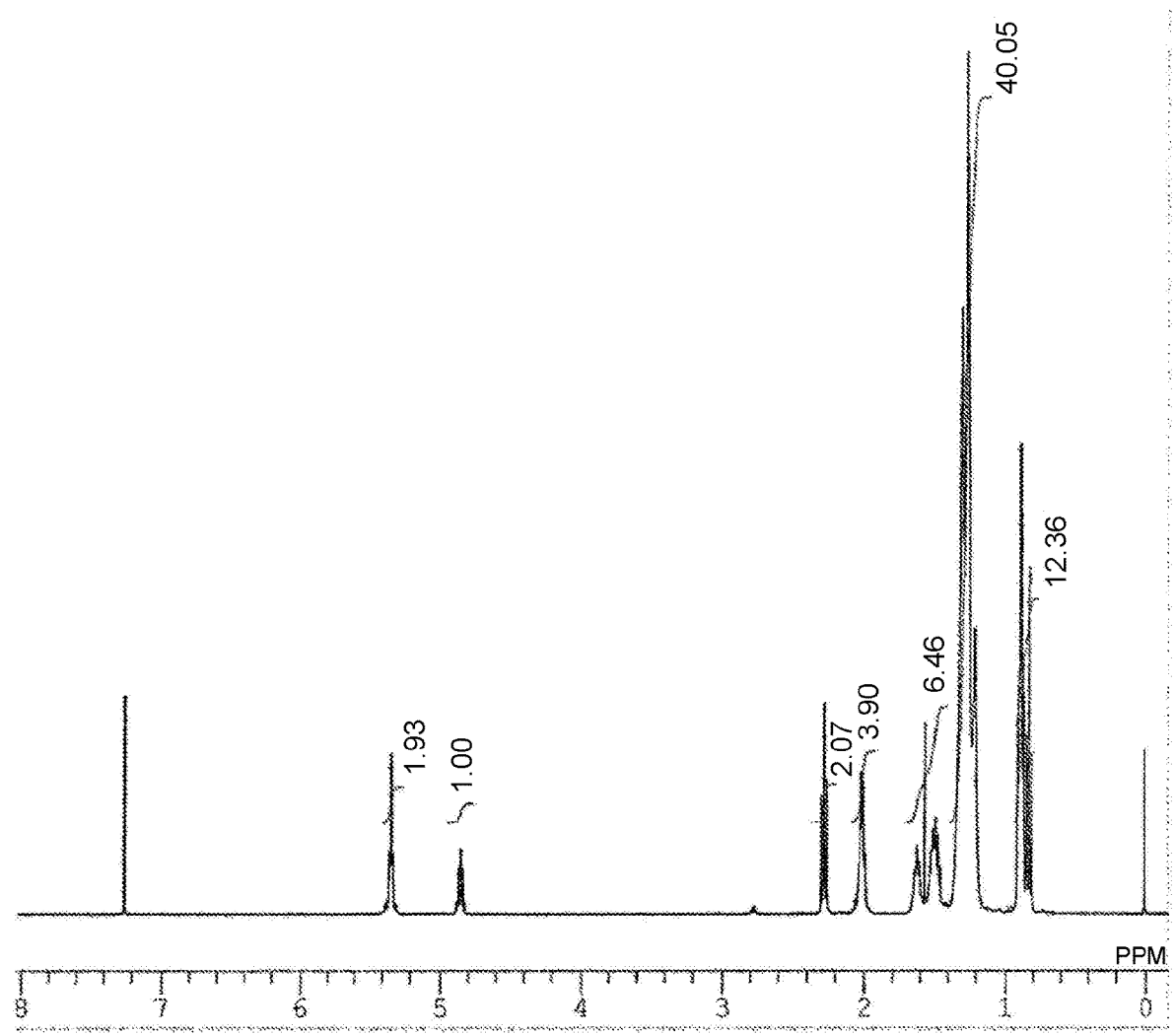
FIG. 6 illustrates a $^1$H-NMR spectrum of 1-hexyl-4-ethyloctyl oleate (12) in Example 8.

Using the same apparatus as for the esterification reaction in Example 1, 110.0 g (389 mmol) of oleic acid (first grade reagent, manufactured by Wako Pure Chemical Industries, Ltd.) and 120.0 g (495 mmol) of 10-ethyl-7-tetradecanol were heated at 200° C. to 210° C. The water generated by the reaction was removed from the Dean-Stark trap. The reaction was carried out for 41 hours. The treatment was performed in the same manner as in Example 5, to obtain 150.0 g (yield: 76%) of compound (12). For this compound, the $^1$H-NMR spectrum is illustrated in FIG. 6.

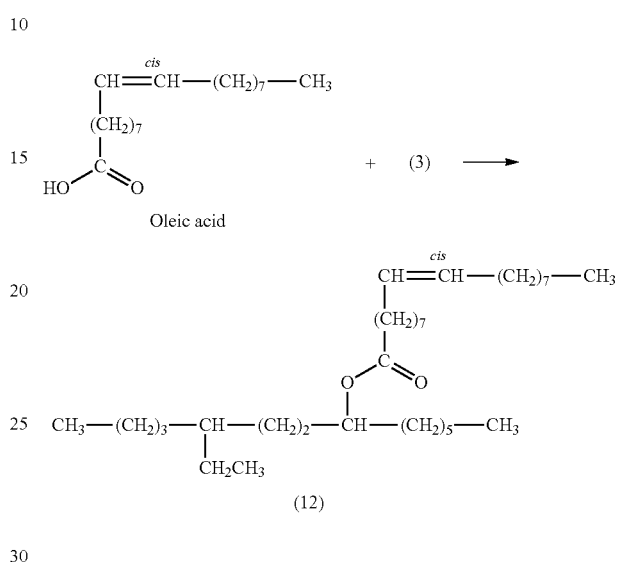

Example 9

Synthesis of bis(1-hexyl-4-ethyloctyl) Adipate (13)

Figure 7:
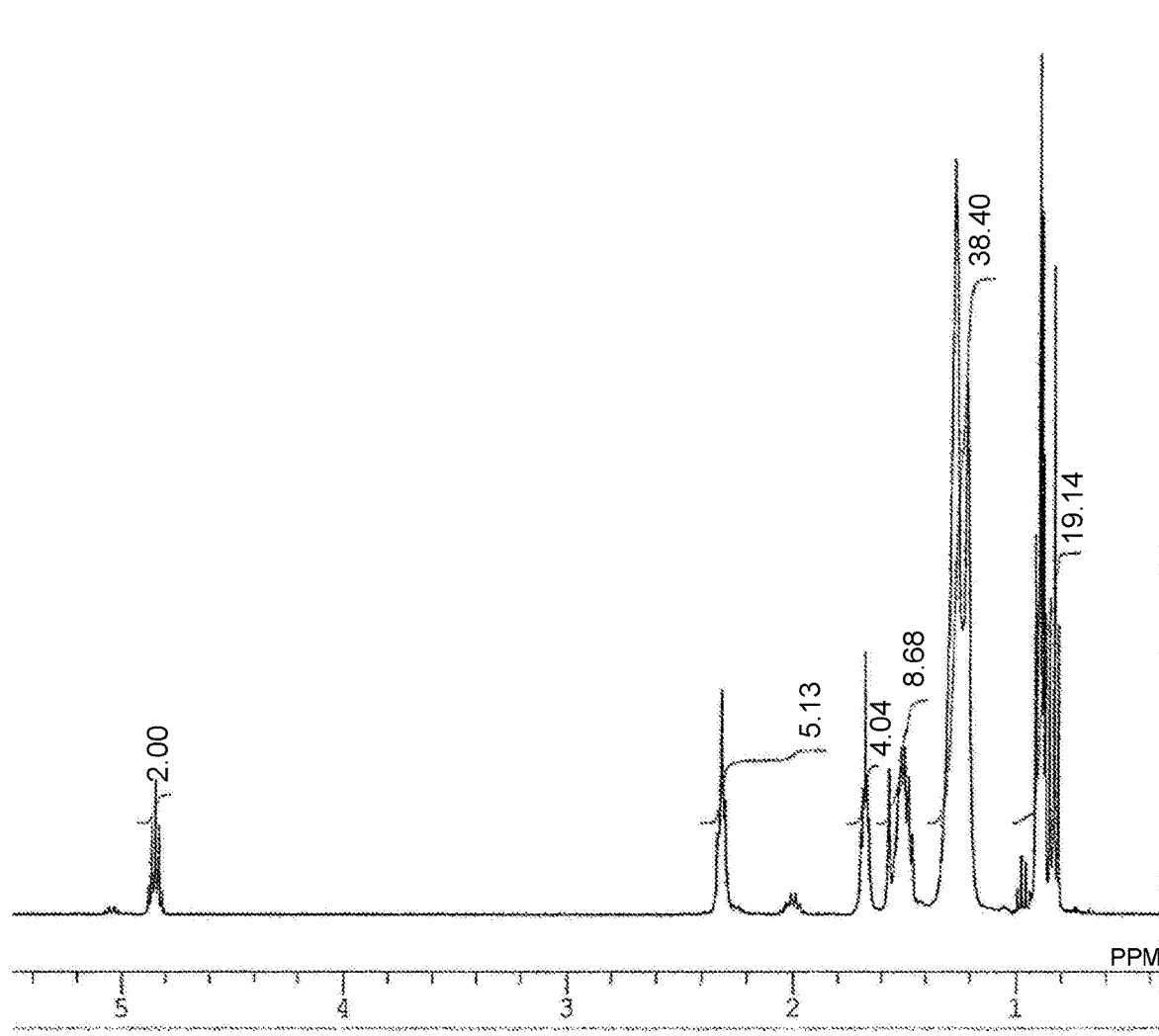
FIG. 7 illustrates a $^1$H-NMR spectrum of bis(1-hexyl-4-ethyloctyl) adipate (13) in Example 9.

Using the same apparatus as for the esterification reaction in Example 1, 65.6 g (449 mmol) of adipic acid (special grade reagent, manufactured by Wako Pure Chemical Industries, Ltd.) and 220.0 g (907 mmol) of 10-ethyl-7-tetradecanol were heated at 210° C. to 220° C. The water generated by the reaction was removed from the Dean-Stark trap. The reaction was carried out for 23 hours. Treatment was performed in the same manner as in Example 5, to obtain 195.0 g (yield: 73%) of compound (13). For this compound, the $^1$H-NMR spectrum is illustrated in FIG. 7.

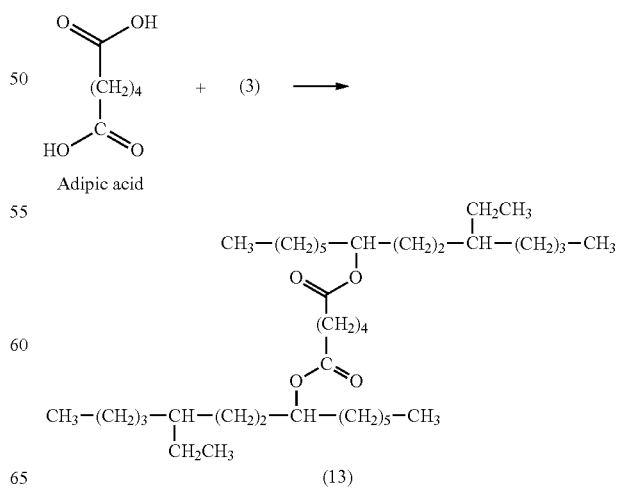

Example 10

Synthesis of 1-(2-ethylhexyl) 6-(1-hexyl-4-ethyloctyl) Adipate (14)

A 2000 mL three-necked flask was equipped with a thermometer, a stirrer, and a Dimroth reflux condenser. To the flask were added 87.6 g (599 mmol) of adipic acid (special grade reagent, manufactured by Wako Pure Chemical Industries, Ltd.), 1404 g (4.8 mol) of 2-ethylhexanol (OA, manufactured by JNC Corporation), 22.3 g (1.2 mol) of water, and 30 mg of hydrochloric acid (special grade reagent, manufactured by Wako Pure Chemical Industries, Ltd.), and the contents were refluxed for 4 hours. The hydrochloric acid was washed with water, and then the unreacted 2-ethylhexanol was distilled off under reduced pressure. GC analysis gave 470 g of ester with a composition ratio of 49% mono-2-ethylhexyl adipate, 46% bis(2-ethylhexyl) adipate, and 5% adipic acid. Using the same apparatus as for the esterification reaction in Example 1, crude mono-2-ethylhexyl adipate and 100 g (371 mmol) of 10-ethyl-7-tetradecanol were heated at 200° C. to 220° C. The water generated by the reaction was removed from the Dean-Stark trap. The reaction was carried out for 20 hours. The treatment was performed in the same manner as in Example 5, and the unreacted compound (3) and bis(2-ethylhexyl) adipate were collected as fractions over 4 hours at a liquid temperature of approximately 230° C. and under a vacuum of approximately 2 torr (270 Pa) in the apparatus. GC analysis showed that the residual liquid after the simple distillation contains 62% compound (14), 15% compound (13), and 22% bis(2-ethylhexyl) adipate. Treatment with activated carbon (SHIRASAGI C) was performed to obtain 205 g of ester.

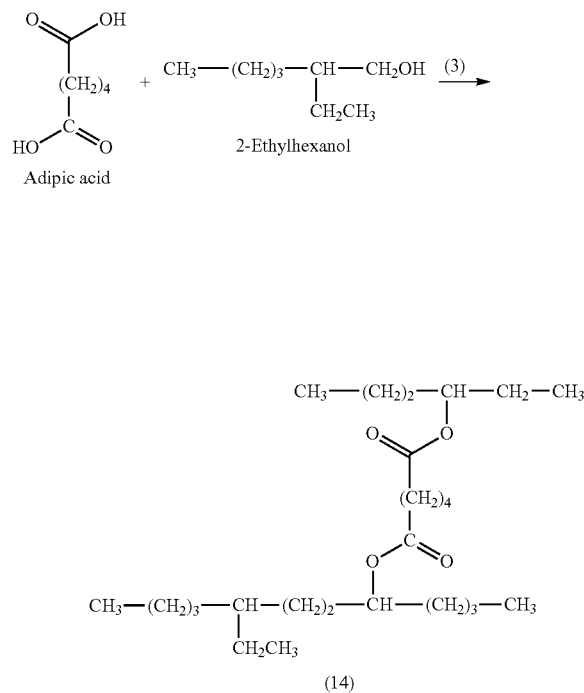

Example 11

Synthesis of bis(1-hexyl-4-ethyloctyl) Terephthalate (15)

A 1,000 mL three-necked flask was equipped with a thermometer, a stirrer, a nitrogen introduction tube, and a Dimroth reflux condenser. To the 1,000 mL three-necked flask were added 50 g (246 mmol) of terephthalic acid chloride (manufactured by Iharanikkei Chemical Industry Co., Ltd.), 180 g (667 mmol) of 10-ethyl-7-tetradecanol, 250 mL of toluene, and 48.3 g (610 mmol) of pyridine, and reaction was allowed to proceed at 60° C. for 4 hours while introducing nitrogen gas. The produced pyridine hydrochloride was filtered and washed with water. Then, the filtrate was transferred to a simple distillation apparatus, and toluene and pyridine were discharged by heating. Further, the unreacted compound (3) was collected as a fraction over 4 hours at a liquid temperature of approximately 230° C. and under a vacuum of approximately 6 torr (800 Pa) in the apparatus. Subsequently, activated carbon (SHIRASAGI C) was added, and stirring was performed at 80° C. for 2 hours. Then, suction filtration was performed to obtain 130 g (yield: 86%) of compound (15).

Figure 8:
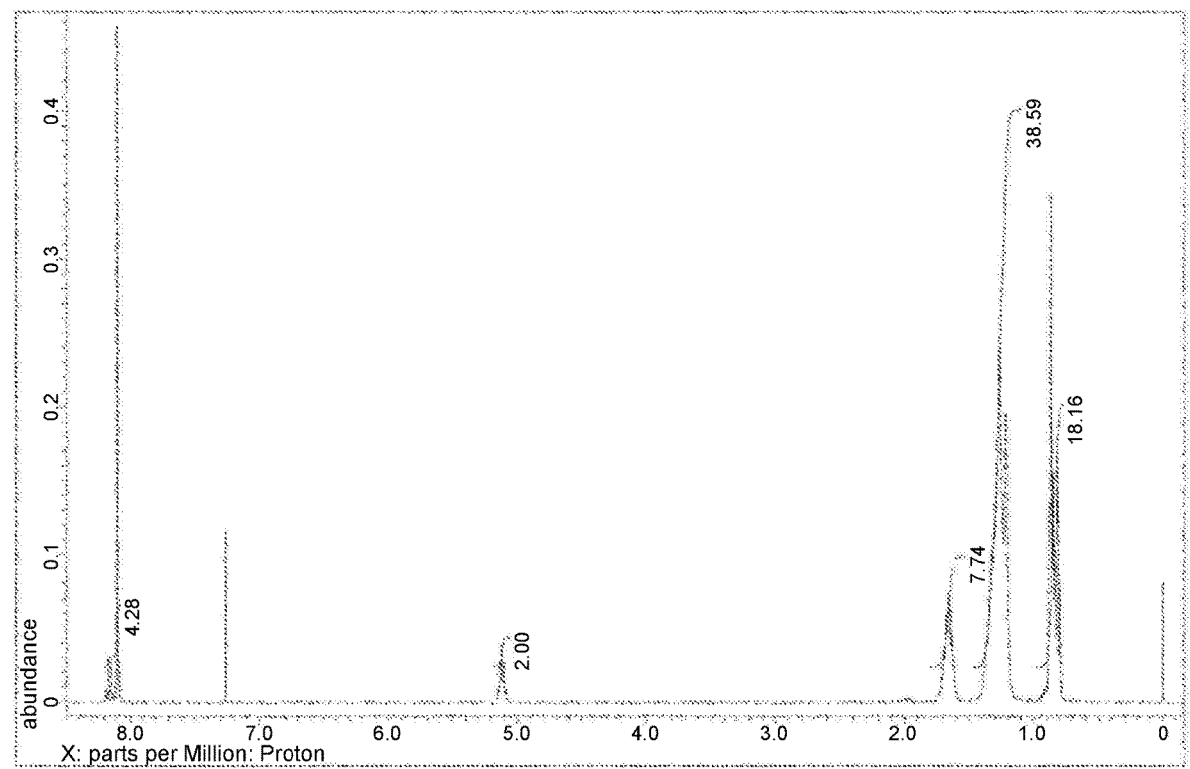
FIG. 8 illustrates a $^1$H-NMR spectrum of bis(1-hexyl-4-ethyloctyl) terephthalate (15) in Example 11.

For this compound, the $^1$H-NMR spectrum is illustrated in FIG. 8.

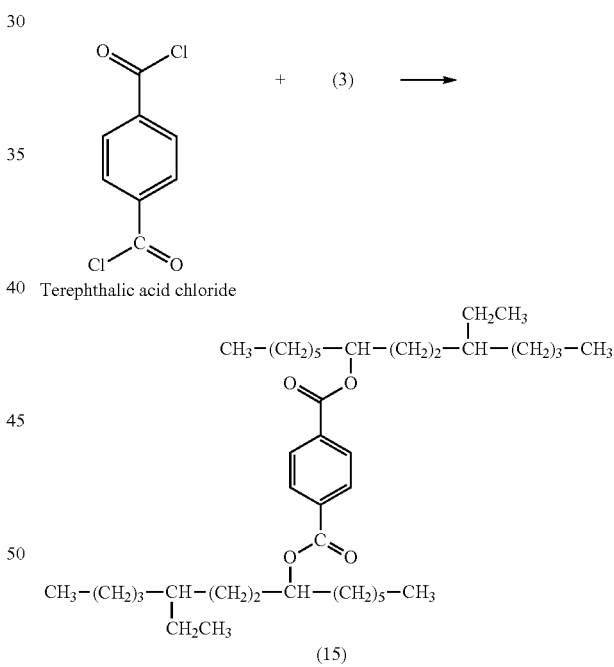

(Measurement results for kinematic viscosity, viscosity index, and pour point)

The kinematic viscosity, viscosity index, and pour point in Examples 1 to 11 and Comparative Example 1 were measured. As shown in Table 1, the ester compounds of Examples 1 to 11 have low viscosity and a sufficiently high viscosity index. In addition, it was shown that the ester compounds of Examples 1 to 11 have a pour point lower than −50° C. and high fluidity at low temperatures, as compared with the ester compound of Comparative Example 1.

TABLE 1

| Example or Comparative Example | Compound name | Compound no. | Kinematic viscosity 40° C. (mm²/s) | Kinematic viscosity 100° C. (mm²/s) | Viscosity index | Pour point (° C.) |
|---|---|---|---|---|---|---|
| Example 1 | 1-Hexyl-4-ethyloctyl decanoate | (4) | 9.654 | 2.607 | 101 | <−50 |
| Example 2 | 1-Hexyl-4-ethyloctyl dodecanoate | (5) | 11.94 | 3.053 | 114 | <−50 |
| Example 3 | 1-Hexyl-4-ethyloctyl tetradecanoate | (6) | 14.53 | 3.552 | 128 | <−50 |
| Example 4 | 1-Hexyl-4-ethyloctyl hexanoate | (7) | 6.325 | 1.919 | 72 | <−50 |
| Comparative Example 1 | 1-Hexadecyl hexanoate | (8) | 7.206 | 2.441 | 190 | 12.5 |
| Example 5 | 1-Hexyl-4-ethyloctyl 2-hexyldecanoate | (9) | 15.96 | 3.565 | 103 | <−50 |
| Example 6 | 1-Hexyl-4-ethyloctyl 2-ethylhexanoate | (10) | 8.326 | 2.201 | 52 | <−50 |
| Example 7 | 1-Hexyl-4-ethyloctyl isostearate | (11) | 23.34 | 4.763 | 126 | <−50 |
| Example 8 | 1-Hexyl-4-ethyloctyl oleate | (12) | 16.01 | 3.981 | 153 | <−50 |
| Example 9 | Bis(1-hexyl-4-ethyloctyl) adipate | (13) | 30.84 | 5.521 | 117 | <−50 |
| Example 10 | 1-(2-Ethylhexyl) 6-(1-hexyl-4-ethyloctyl) adipate | (14) | 18.18 | 3.977 | 116 | <−50 |
| Example 11 | Bis(1-hexyl-4-ethyloctyl) terephthalate | (15) | 168.8 | 15.66 | 94 | −45 |

INDUSTRIAL APPLICABILITY

The ester compound of the present invention has excellent fluidity at low temperatures and a good pour point, which allows it to be suitably used as a lubricating oil base oil.

What is claimed is:

1. An ester compound represented by Formula (I):

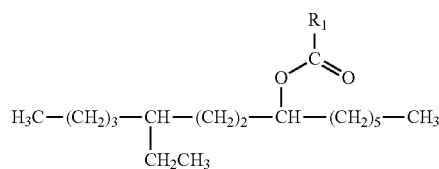

in Formula (I), $R_1$ is a hydrocarbon group having 1 to 35 carbon atoms, and at least one hydrogen in the hydrocarbon group may be independently substituted with a group represented by Formula (II);

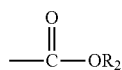

in Formula (II), $R_2$ is a linear alkyl having 1 to 30 carbon atoms or a branched alkyl having 3 to 30 carbon atoms.

2. The ester compound according to claim 1, which is represented by Formula (I):

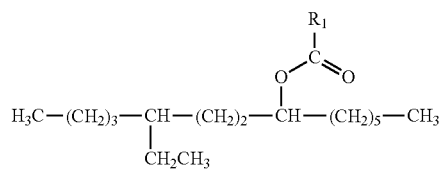

in Formula (I), $R_1$ is a linear alkyl having 1 to 35 carbon atoms, a branched alkyl having 3 to 35 carbon atoms, or a linear alkenyl having 4 to 24 carbon atoms, in which at least one hydrogen in the alkyl and the alkenyl may be independently substituted with a group represented by Formula (II);

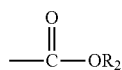

in Formula (II), $R_2$ is a linear alkyl having 1 to 30 carbon atoms or a branched alkyl having 3 to 30 carbon atoms.

3. The ester compound according to claim 1, which is represented by Formula (I):

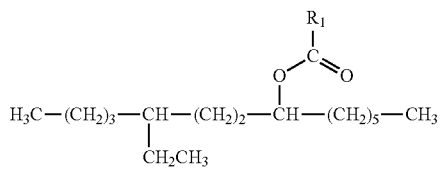

in Formula (I), $R_1$ is phenyl, cyclohexyl, or cyclohexenyl, in which at least one hydrogen in these rings may be independently substituted with a linear alkyl having 1 to 10 carbon atoms or a group represented by Formula (II);

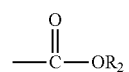

in Formula (II), $R_2$ is a linear alkyl having 1 to 30 carbon atoms or a branched alkyl having 3 to 30 carbon atoms.

4. The ester compound according to claim 1,
wherein at least one hydrogen in $R_1$ is substituted with a group represented by Formula (II), and
$R_2$ is a group represented by Formula (III):

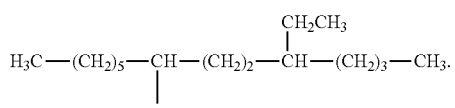

5. A lubricating oil base oil, comprising:
the ester compound according to claim 1.

6. A method for producing the ester compound according to claim 1, the method comprising:
a step of subjecting 10-ethyl-7-tetradecanol and carboxylic acid to esterification reaction.

7. The ester compound according to claim 2,
wherein at least one hydrogen in $R_1$ is substituted with a group represented by Formula (II), and
$R_2$ is a group represented by Formula (III):

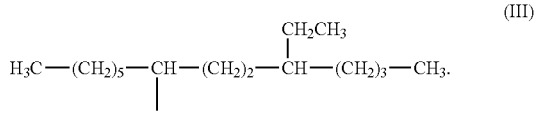
(III)

8. The ester compound according to claim 3,
wherein at least one hydrogen in $R_1$ is substituted with a group represented by Formula (II), and
$R_2$ is a group represented by Formula (III):

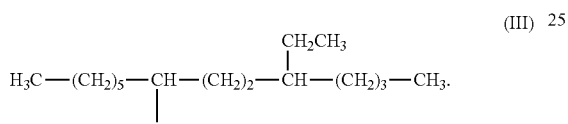
(III)

9. A lubricating oil base oil, comprising:
the ester compound according to claim 2.

10. A lubricating oil base oil, comprising:
the ester compound according to claim 3.

11. A lubricating oil base oil, comprising:
the ester compound according to claim 4.

12. A lubricating oil base oil, comprising:
the ester compound according to claim 7.

13. A lubricating oil base oil, comprising:
the ester compound according to claim 8.

14. A method for producing the ester compound according to claim 2, the method comprising:
a step of subjecting 10-ethyl-7-tetradecanol and carboxylic acid to esterification reaction.

15. A method for producing the ester compound according to claim 3, the method comprising:
a step of subjecting 10-ethyl-7-tetradecanol and carboxylic acid to esterification reaction.

16. A method for producing the ester compound according to claim 4, the method comprising:
a step of subjecting 10-ethyl-7-tetradecanol and carboxylic acid to esterification reaction.

17. A method for producing the ester compound according to claim 7, the method comprising:
a step of subjecting 10-ethyl-7-tetradecanol and carboxylic acid to esterification reaction.

18. A method for producing the ester compound according to claim 8, the method comprising:
a step of subjecting 10-ethyl-7-tetradecanol and carboxylic acid to esterification reaction.

* * * * *